United States Patent

Rosenberg et al.

[11] Patent Number: 6,009,690
[45] Date of Patent: Jan. 4, 2000

[54] PROCESS AND APPARATUS FOR THE PRODUCTION OF DIVISIBLE TABLETS

[75] Inventors: Joerg Rosenberg, Ellerstadt; Werner Maier, Schifferstadt; Helmut Fricke, Mutterstadt; Jörg Breitenbach, Mannheim, all of Germany

[73] Assignee: BASF Aktiengesellschaft, Ludwigshafen, Germany

[21] Appl. No.: 08/849,900

[22] PCT Filed: Dec. 22, 1995

[86] PCT No.: PCT/EP95/05117

§ 371 Date: Jun. 18, 1997

§ 102(e) Date: Jun. 18, 1997

[87] PCT Pub. No.: WO96/19962

PCT Pub. Date: Jul. 4, 1996

[30] Foreign Application Priority Data

Dec. 23, 1994 [DE] Germany ............... 44 46 470

[51] Int. Cl.[7] .............. A61K 9/44; B29C 43/08
[52] U.S. Cl. ............... 53/454; 53/560; 53/900; 264/167; 264/175; 264/266; 264/280; 425/363; 424/467
[58] Field of Search ............... 264/175, 280, 264/167, 266, DIG. 37; 425/363; 424/467; 53/453, 454, 559, 560, 900

[56] References Cited

U.S. PATENT DOCUMENTS

| | | | |
|---|---|---|---|
| D. 216,307 | 12/1969 | Ninger | 424/467 |
| 2,152,101 | 3/1939 | Scherer | 264/DIG. 37 |
| 2,219,578 | 8/1940 | Pittenger | 264/DIG. 37 |
| 2,566,628 | 9/1951 | Patt | 425/363 |
| 3,927,194 | 12/1975 | Geller | 424/467 |
| 4,215,104 | 7/1980 | Ullman et al. | 424/467 |
| 4,880,585 | 11/1989 | Klimesch et al. | 264/167 |
| 5,009,896 | 4/1991 | Becker | 424/467 |
| 5,049,333 | 9/1991 | Wolfe et al. | 425/363 |
| 5,520,929 | 5/1996 | Makino et al. | 424/467 |

FOREIGN PATENT DOCUMENTS

| | | |
|---|---|---|
| 232863 | 3/1911 | Germany . |
| 683066 | 1/1994 | Switzerland . |

*Primary Examiner*—Ian H. Silbaugh
*Assistant Examiner*—Dae Young Lee
*Attorney, Agent, or Firm*—Keil & Weinkauf

[57] ABSTRACT

A process for the production of divisible tablets by melt calendering in which two molding rolls are combined together, at least one of which has depressions with at least one bar which extends up to the surface line of the molding roll and forms a score.

9 Claims, 3 Drawing Sheets

PROCESS AND APPARATUS FOR THE PRODUCTION OF DIVISIBLE TABLETS

The present invention relates to a process for the production of divisible tablets by molding a melt which contains an active ingredient in a calender with counter-rotating molding rolls which have on their surface depressions for receiving and molding the tablet composition (melt calendering).

The production of tablets by calendering a melt containing an active ingredient is disclosed in DE-A 1 766 546 and U.S. Pat. No. 4,880,585. The basis of this process is the embedding of an active ingredient in a melt of a carrier, eg. fatty substances or water-soluble thermoplastic polymers. The melt is produced by melting the mixture of active ingredient, polymer and, where appropriate, other ancillary substances, for example in an extruder, and molding the melt in a downstream molding calender to give tablets, which harden on cooling. The molding calender comprises a pair of counter-rotating molding rolls which have on their surface corresponding engravings (depressions) which correspond to the shape of one half of the required tablet. The tablet molding takes place in the region of contact of the two rolls by combination of the tablet composition in one depression on one roll with that in the opposite depression on the other roll. Calendering of the melt containing an active ingredient as disclosed in U.S. Pat. No. 4,880,585 took place using a pair of molding rolls with identical depressions. In this way each molding roll provides an identically shaped half of the tablet so that the resulting tablets are symmetrical.

It is often desirable for tablets to be divisible in order to be able to alter the dosage without the need to produce individual tablets for each particular dosage. However, the production of divisible tablets by calendering has met with considerable difficulty. Attempts have been made to provide the molding rolls with depressions which afford tablets which are visually identical to the divisible tablets produced by conventional tableting techniques. This has been brought about by leaving, when cutting out the depressions, a small rib, often in the micrometer range, in the middle of the bottom of each depression, which leads to formation of what is called the score (on each half of the tablet, on both sides) in the finished tablets. However, the manufacture of such molding rolls entails a considerable increase in cost. This is because, after the depressions have been cut out, a polishing is necessary to smooth the surface. This is possible in such a case only manually and meets with considerable difficulties because of the ribs present in the depressions.

It is an object of the present invention to provide a process for the production of divisible tablets by melt calendering which can be implemented in a simple and cost-saving manner.

We have found that this object is achieved by combining two molding rolls together, at least one of which has depressions which are separated from one another by at least one bar which extends essentially as far as the surface line.

The present invention therefore relates to a process for the production of divisible tablets by molding a melt containing an active ingredient in a calender with two counter-rotating molding rolls which have depressions for receiving and molding the melt to tablets, wherein at least one molding roll in which the depressions are divided by at least one bar which extends essentially as far as the surface line of the molding roll, and forms a score, is used.

The tablets are formed by combination of the depressions on the first molding roll with the corresponding depressions on the second molding roll. The bar present in the depressions is relatively narrow and leads to formation of the score on molding of the tablets.

In a preferred embodiment there is use of a first molding roll in which the depressions are divided by n bars, and a second molding roll with corresponding depressions divided by n' bars. In this case, n' is in the range from 0 to n−1.

The number n of bars in the depressions on the first roll depends on the number of parts the tablets are to be divisible into. In the simplest and commonest case, this number will be one (n=1). If a tablet half obtained therewith is combined with a tablet half resulting from a depression with n'=n−1=0, ie. no bar, on the second roll, the result is a tablet which can be divided into two parts. Normally, the bar divides the depressions on the first roll into two equal parts (essentially mirror-image identical) so that the resulting tablet can be divided into two equal parts. The two parts of a depression on the first roll can, however, also be different, ie. the result in this case is a tablet which can be divided into two different parts, for example one part can comprise ⅓ and the other can comprise ⅔ of the tablet, so that it is also possible conveniently to administer ⅓ or ⅔ of the amount of active ingredient contained in the tablet. This embodiment with n=1 and n'=0 is particularly advantageous for producing divisible oblong tablets and lenticular tablets.

The number of bars n' in a depression on the second molding roll is not more than n−1. This number can, however, also be lower and is therefore in the range from 0 to n−1. For example, depressions with two bars (n=2) on the first molding roll can be provided for combination with corresponding depressions without bar or with one bar on the second molding roll (n'=0 or 1). The result in this case is a tablet which can be divided into three, or a tablet which can be both divided into three (n=2; n'=0) and halved (n=2; n'=1).

Depending on the contact pressure of the molding rolls it is possible to produce a "chain" of two, three or more tablets, from which any required number can be taken off in order to alter the dosage, or (with a higher contact pressure) individual divisible tablets.

In a particularly preferred embodiment, the second molding roll is a smooth roll, ie. it has no depressions. It is possible in this way to bring about a substantial alteration in the dosage at a given concentration of active ingredient in the melt by altering the number of bars in the depressions on the first roll. In order to obtain divisible tablets, either the bar terminates a short distance below the surface of the molding roll, or the contact pressure between the two molding rolls is relatively low, or there is in fact a small distance between the molding rolls (eg. 0.1–1 mm) when the bar extends up to the surface.

The latter embodiment moreover has advantages compared with all the others based on a combination of two molding rolls with depressions. In the production of tablets by means of two molding rolls with depressions, the latter must in each case be exactly opposite to one another so that the tablet halves which are formed are not displaced with respect to one another, which makes great demands on the precision of production of the depressions and of rotation of the molding rolls. The displacement problem does not, by contrast, occur with a combination with one smooth molding roll because, in this case, there are not two tablet halves which might be displaced with respect to one another. This embodiment is therefore particularly suitable for smaller tablet forms in which even very small inaccuracies in managing the calendering molding rolls have very great effects on the appearance of the tablets.

The tablets are produced starting from a mixture which contains one or more pharmaceutical active ingredients and one or more conventional ancillary substances and which becomes a paste or viscous liquid, and can therefore be extruded, by melting or softening of at least one component.

These are, in particular, mixtures containing pharmacologically acceptable polymers (with the glass transition temperature of the mixture being below the decomposition temperature of all the components of the mixture), for example polyvinylpyrrolidone (PVP), copolymers of N-vinylpyrrolidone (NVP) and vinyl acetate, copolymers of vinyl acetate and crotonic acid, partially hydrolyzed polyvinyl acetate, polyvinyl alcohol, ethylene/vinyl acetate copolymers, poly(hydroxyethyl methacrylate), copolymers of methyl methacrylate and acrylic acid, cellulose esters, cellulose ethers, polyethylene glycol or polyethylene, preferably NVP copolymers with vinyl acetate, hydroxypropylcellulose and polyethylene glycols/polyethylene oxides. The K values (H. Fikentscher, Cellulose-Chemie 13 (1932) 58–64 and 71–74) of the polymers are in the range from 10 to 100, preferably 12 to 70, in particular 12 to 35, for PVP preferably 12–35, in particular 12–17.

The polymeric binder must soften or melt in the complete mixture of all the components in the range from 50 to 180, preferably 60 to 130° C., so that the composition can be extruded. The glass transition temperature of the mixture must therefore always be below 180, preferably below 130° C. It is if necessary reduced by conventional pharmacologically acceptable plasticizing ancillary substances such as long-chain alcohols, ethylene glycol, propylene glycol, trimethylolpropane, triethylene glcyol, butanediols, pentanols, hexanols, polyethylene glycols, silicones, aromatic carboxylic esters (eg. dialkyl phthalates, trimellitic esters, benzoic esters, terephthalic esters) or aliphatic dicarboxylic esters (eg. dialkyl adipates, sebacic esters, azelaic esters, citric and tartaric esters) or fatty acid esters.

Examples of conventional pharmaceutical ancillary substances, whose total amount can be up to 100% by weight based on the polymer, are extenders such as silicates or diatomaceous earth, stearic acid or salts thereof, eg. the magnesium or calcium salt, methylcellulose, sodium carboxymethylcellulose, talc, sucrose, lactose, cereal or corn starch, potato flour, polyvinyl alcohol, also wetting agents, preservatives, disintegrants, absorbents, colorants, flavorings (cf., for example, H. Sucker et al. Pharmazeutische Technologie, Thieme-Verlag, Stuttgart 1978).

Pharmaceutical active ingredients mean for the purpose of the invention all substances with a pharmaceutical effect and minimal side effects as long as they do not decompose under the processing conditions. The amount of active ingredient per dose unit and the concentration may vary within wide limits depending on the activity and rate of release. The only condition is that they suffice to achieve the desired effect. Thus, the concentration of active ingredient can be in the range from 0.1 to 95, preferably from 20 to 80, in particular 30 to 70, % by weight. It is also possible to use combinations of active ingredients. Active ingredients for the purpose of the invention are also vitamins and minerals, as well as crop treatment agents and insecticides.

The process according to the invention is suitable, for example, for processing the following active ingredients:

acebutolol, acetylcysteine, acetylsalicylic acid, acyclovir, alprazolam, alfacalcidol, allantoin, allopurinol, ambroxol, amikacin, amiloride, aminoacetic acid, amiodarone, amitriptyline, amlodipine, amoxicillin, ampicillin, ascorbic acid, aspartame, astemizole, atenolol, beclomethasone, benserazide, benzalkonium hydroxide, benzocaine, benzoic acid, betamethasone, bezafibrate, biotin, biperiden, bisoprolol, prazosin, bromazepam, bromhexine, bromocriptine, budesonide, bufexamac, buflomedil, buspirone, caffeine, camphor, captopril, carbamazepine, carbidopa, carboplatin, carotenoids such as β-carotene or canthaxanthin, cefachlor, cefalexin, cefatroxil, cefazolin, cefixime, cefotaxime, ceftazidime, ceftriaxone, cefuroxime, celedilin, chloramphenicol, chlorhexidine, chlorpheniramine, chlortalidone, choline, cyclosporin, cilastatin, cimetidine, ciprofloxacin, cisapride, cisplatin, clarithromycin, clavulanic acid, clomipramine, clonazepam, clonidine, clotrimazole, codeine, cholestyramine, cromoglycic acid, cyanocobalamin, cyproterone, desogestrel, dexamethasone, dexpanthenol, dextromethorphan, dextropropoxiphene, diazepam, diclofenac, digoxin, dihydrocodeine, dihydroergotamine, diltiazem, diphenhydramine, dipyridamole, dipyrone, disopyramide, domperidone, dopamine, enalapril, ephedrine, epinephrine, ergocalciferol, ergotamine, erythromycin, estradiol, ethinylestradiol, etoposide, Eucalyptus globulus, famotidine, felodipine, fenofibrate, fenoterol, fentanyl, flavin mononucleotide, fluconazole, flunarizine, fluorouracil, fluoxetine, flurbiprofen, furosemide, gemfibrozil, gentamicin, Ginkgo biloba, glibenclamide, glipizide, clozapine, Glycyrrhiza glabra, guaifenesin, haloperidol, heparin, hyaluronic acid, hydrochlorothiazide, hydrocodone, hydrocortisone, hydromorphone, ipratropium hydroxide, ibuprofen, imipenem, indomethacin, iohexol, iopamidol, isosorbide dinitrate, isosorbide mononitrate, isotretinoin, ketotifen, ketoconazole, ketoprofen, ketorolac, labetalol, lactulose, lecithin, levocarnitine, levodopa, levoglutamide, levonorgestrel, levothyroxine, lidocaine, lipase, lipoic acid, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, multivitamin mixtures or combinations and mineral salts, N-methylephedrine, naftidrofuryl, naproxen, neomycin, nicardipine, nicergoline, nicotinamide, nicotine, nicotinic acid, nifedipine, nimodipine, nitrendipine, nizatidine, norethisterone, norfloxacin, norgestrel, nortriptyline, nystatin, ofloxacin, omeprazole, ondansetron, pancreatin, panthenol, pantothenic acid, paracetamol, penicillin G, penicillin V, phenobarbital, pentoxifylline, phenylephrine, phenylpropanolamine, phenytoin, piroxicam, polymyxin B, povidone-iodine, pravastatin, prednisolone, bromocriptine, propafenone, propranolol, pseudoephedrine, pyridoxine, quinidine, ramipril, ranitidine, reserpine, retinol, riboflavin, rifampicin, rutoside, saccharin, salbutamol, salcatonin, salicylic acid, simvastatin, somatropin, sotalol, spironolactone, sucralfate, sulbactam, sulfamethoxazole, sulpiride, tamoxifen, tegafur, teprenone, terazosin, terbutaline, terfenadine, theophylline, thiamine, ticlopidine, timolol, tranexamic acid, tretinoin, triamcinolone acetonide, triamterene, trimethoprim, troxerutin, uracil, valproic acid, vancomycin, verapamil, vitamins $B_1$, $B_2$, $B_4$, $B_6$, $B_{12}$, $D_3$, E, K, folinic acid, zidovudine.

In a few cases, solid solutions may form. The term "solid solutions" is familiar to the skilled person, for example from the literature cited at the outset. In solid solutions of pharmaceutically active ingredients in polymers, the active ingredient is present in a molecular dispersion in the polymer.

The pharmaceutical mixture is then melted in a conventional way, preferably in an extruder, and fed to the molding calender as described, for example, in U.S. Pat. No. 4,880, 585. If necessary, the tablets are cooled after the calendering, eg. in an air or cooling bath.

In the case of sticky or highly viscous materials which are detached from the mold only with difficulty or not at all, it is expedient to use a mold release agent, for example a silicone oil, silicone paint, triglyceride or lecithin.

The tablets can, if required, be provided with a covering, in particular to mask the taste or to make the tablets distinguishable by color or for packaging. For this purpose, the melt containing active ingredient is fed between two sheets of the covering material into the molding rolls.

The covering material can be selected from a wide range of materials. The only requirement is that the material is pharmaceutically acceptable.

Covering materials which are suitable for producing film-coated tablets and which rapidly dissolve in the acidic gastric fluid are sheets of, for example, gelatin, polyvinyl alcohol, alkylcelluloses such as methylcelluloses, hydroxyalkylcelluloses such as hydroxyethyl-, hydroxypropyl- or hydroxypropylmethylcellulose, polyvinylpyrrolidone, certain acrylic resins such as copolymers based on dimethylaminoethyl methacrylate and methacrylates (Eudragit E) etc.

The covering material can, if required, contain a colorant or a pigment or else another active ingredient.

In another embodiment, the sheets used are those suitable for packaging the tablets. These are, in particular, water-insoluble thermoforming sheets, the preferred material being polyethylene, polypropylene, polyvinyl chloride, polyethylene terephthalate, polystyrene, aluminum or coated aluminum. The tablets are in this way immediately sealed in a blister pack. The separate packaging step which is otherwise customary is thus unnecessary and, moreover, it is possible in this way to pack the tablets aseptically in an extremely simple manner, especially when care is taken that the outer edges of the tablet strip are sealed airtight.

It has emerged that there is not, as expected, vigorous adhesion of the hot tablet composition to the water-insoluble thermoforming sheet so that later removal of the tablets from the pack would be impeded or even impossible.

It has proven particularly advantageous for packaging the tablets to combine a molding roll with the depressions for receiving and molding the tablet composition with a smooth roll. This results in "half" tablets which are sealed in a blister pack which has on one side depressions for receiving the tablets and is closed on the other side with a smooth sheet which can be pulled off. In this case, an aluminum sheet or a sheet of coated aluminum has proven particularly expedient for closing the pack.

It may also prove to be expedient not to allow the packaged tablets to cool in air, as otherwise usual, but to provide a separate cooling step. Suitable for this purpose is a water bath, stream of cold air etc. This prevents the tablets in the pack cooling too slowly, which may lead to subsequent deformation of the tablets.

It is also possible to use the sheets for the film coating of the tablets and the sheets for the blister-packaging of the tablets simultaneously. In this case, the melt in the molding rolls is covered by the sheet for the film coating and simultaneously sealed in the packaging sheet.

The shape of the depressions, and thus of the tablets obtainable according to the invention, can be chosen substantially as desired. Besides the oblong tablets already mentioned, lenticular tablets have proven to be particularly expedient. The molding rolls used to produce them have depressions in the shape of segments of an ellipsoid, in particular of a sphere. The angle between the tangential surface of the depressions at the upper edge and the tangential surface of the molding roll (at the intersection between the depression and the surface of the roll) is <90°, preferably <45°, in this case. The lenticular tablets have the advantage that deflashing thereof is particularly easy.

The present invention also relates to an appliance (calender) for carrying out the process according to the invention with two counter-rotating molding rolls which are in contact where appropriate along a surface line and have depressions for receiving and molding the melt to tablets, wherein at least one molding roll has depressions which are divided by at least one bar which extends essentially up to the surface of the molding roll and forms a score.

In general, said bar extends up to the surface of the molding roll. However, in some cases, it may be expedient for the bar not to extend completely to the surface line, i.e. it terminates a short distance below the surface line. This increases the stability of the resulting tablet.

In a preferred embodiment, the first molding roll has depressions which are divided by n bars, while the corresponding depressions on the second molding roll are divided by n' bars, where n' is in the range from 0 to n−1.

The depressions on the second molding roll are expediently deeper than those on the first molding roll. The result is then asymmetric tablets in which the "half" without score is larger than the "half" with score. The risk of breakage during packaging or on inappropriate handling is considerably less with tablets of this type.

A first molding roll which has depressions with a bar is preferably combined with a second molding roll which has a corresponding depression without bar.

In another embodiment, a first molding roll which has depressions with two bars (n=2) is combined with a second molding roll which has corresponding depressions without bar (n'=0) or with one bar (n'=1).

In a particularly preferred embodiment, a first molding roll which has depressions with at least one bar is combined with a smooth roll.

The invention is explained in detail hereinafter by means of the drawing and the examples.

BRIEF DESCRIPTION OF THE FIGURES

FIG. 1 shows a prior art molding roll 1. It has depressions 2 for receiving and molding the molten tablet composition to tablets. At the bottom of these depressions there are ribs 3 which are perpendicular to the longitudinal axis of the molding rolls and which have been left on cutting out the depressions. Combining together two such prior art molding rolls 1 and producing tablets by melt calendering results in elongate tablets 4, called oblong tablets of the type shown in FIG. 2. These tablets have a score 5 which allows the tablet to be broken into two equal parts.

FIG. 3 shows a combination according to the invention of a first molding roll 6 with a second molding roll 8. The molding roll 6 has three identical, immediately adjacent depressions 2. These depressions are each divided by a bar 7 which extends to the surface of the molding roll 6. The second molding roll 8 likewise has three directly adjacent depressions 2 of corresponding shape. In the case shown, all the depressions 2 are separated from one another only by a narrow flash 13 which, in the case shown, essentially corresponds to the bar 7. However, it is also possible for a larger space, ie. a wider flash 13, to lie between the depressions 2 used to form a tablet.

The peripheral line around the depressions 2 in the molding roll 6 (in the surface of the molding roll) corresponds to the peripheral line around the depressions in the molding roll 8, ie. the base areas of the resulting tablet halves correspond to one another, so that the two halves can be joined together to give a tablet.

Figure 4:
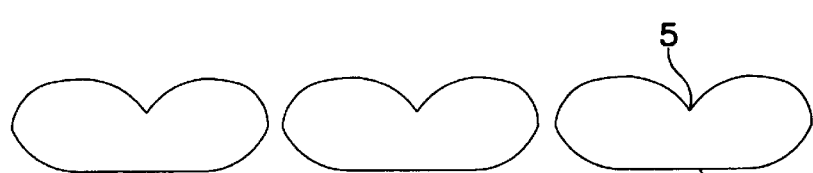
FIG. 4 shows a section through tablets obtained with the pair of molding rolls shown in FIG. 3.

This results in divisible tablets 9 of the type shown in FIG. 4. They have a score 5 which makes it possible to divide the tablets into two equal halves.

Figure 5:
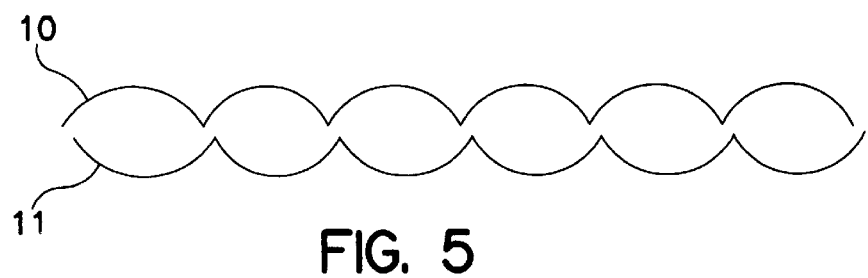
FIG. 5 shows a section through tablets with a displacement between the two tablet halves.

As mentioned above, the precision in the production and rotation of the molding rolls must be very great in order to avoid displacement between the upper and lower halves of the tablet. A displacement of this type between tablet halves 10 and 11 is shown in FIG. 5. Such a displacement between the tablet halves is avoided with the combination, shown in FIG. 6, of a first molding roll 6 with five bars 7 with a second molding roll 8 which is designed as smooth roll. The combination of molding rolls shown in FIG. 6 results, with a relatively low contact pressure or with a small distance between the molding rolls, in a "chain" of "half tablets" 12 of the type shown in FIG. 7. It is possible for this type of tablets in particular to be produced with very small dimensions so that the dosage can be varied within a wide range by the choice of the size of the depressions and the length of the "chain" of the tablets.

EXAMPLE 1

A mixture of 60.0% by weight of Kollidon VA-64 (BASF) (polyvinylpyrrolidone copolymer with vinyl acetate (60:40)) and 40.0% by weight of lactose monohydrate was extruded in a twin screw extruder (ZSK-40, Werner+Pfleiderer) under the following conditions:

| Temperatures: | |
|---|---|
| Shot 1: | 80° C. |
| Shot 2: | 100° C. |
| Shot 3: | 130° C. |
| Shot 4: | 130° C. |
| Dies: | 135° C. |
| Material throughput: | 25 kg/h |
| Screw speed: | 160 rpm |

Figure 1:
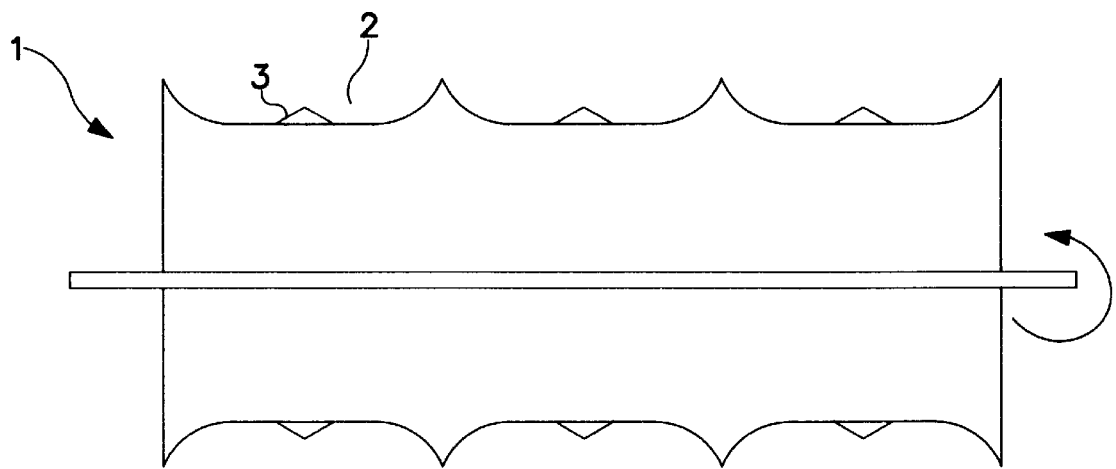
FIG. 1 shows a cross-section through a prior art molding roll for producing divisible tablets.
Figure 2:
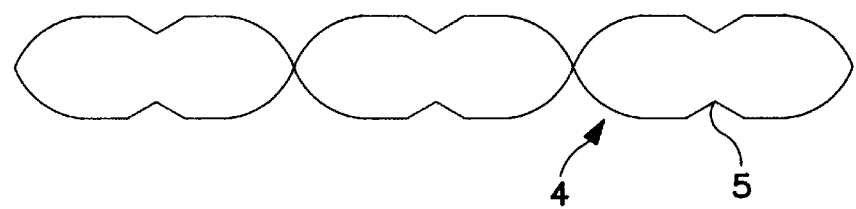
FIG. 2 shows a section through oblong tablets obtained with the molding roll shown in FIG. 1.
Figure 3:
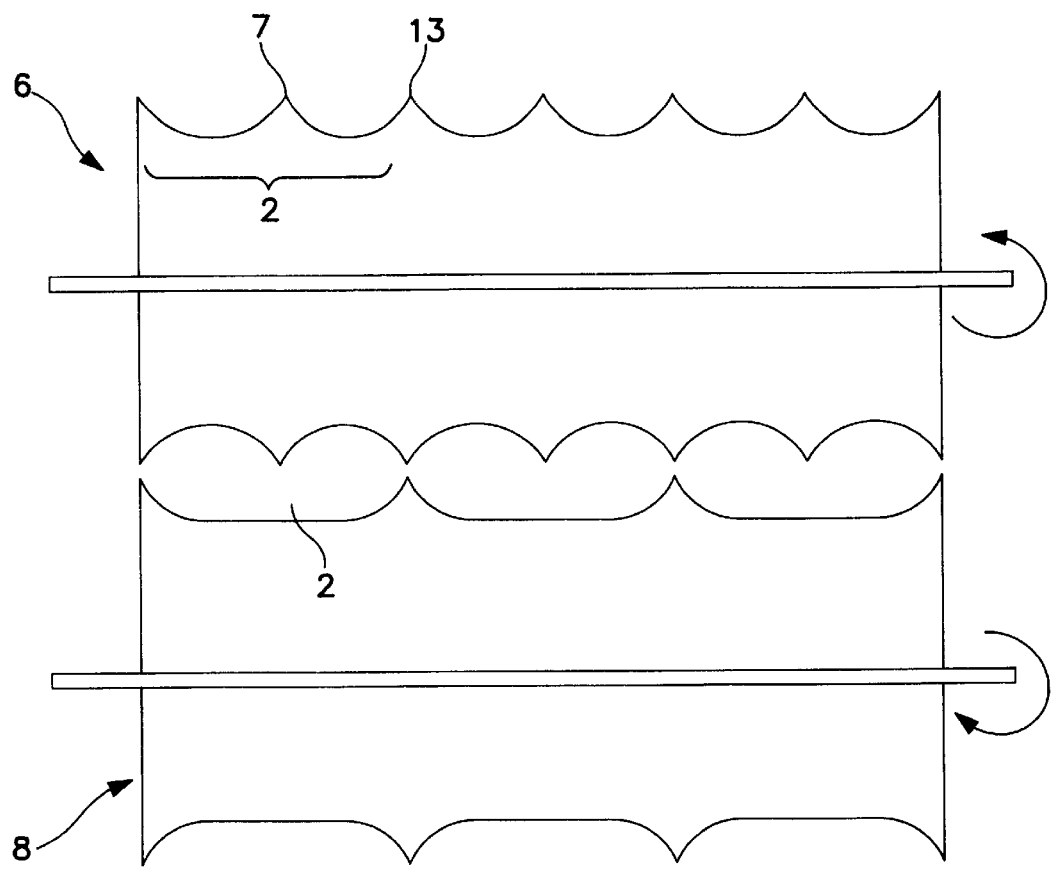
FIG. 3 shows a cross-section through a pair of molding rolls according to the present invention.

The melt was fed into a molding calender with two molding rolls of the type shown in FIG. 3. This resulted in tablets as depicted in FIG. 4. They could be easily and smoothly broken into two equal halves.

Figure 6:
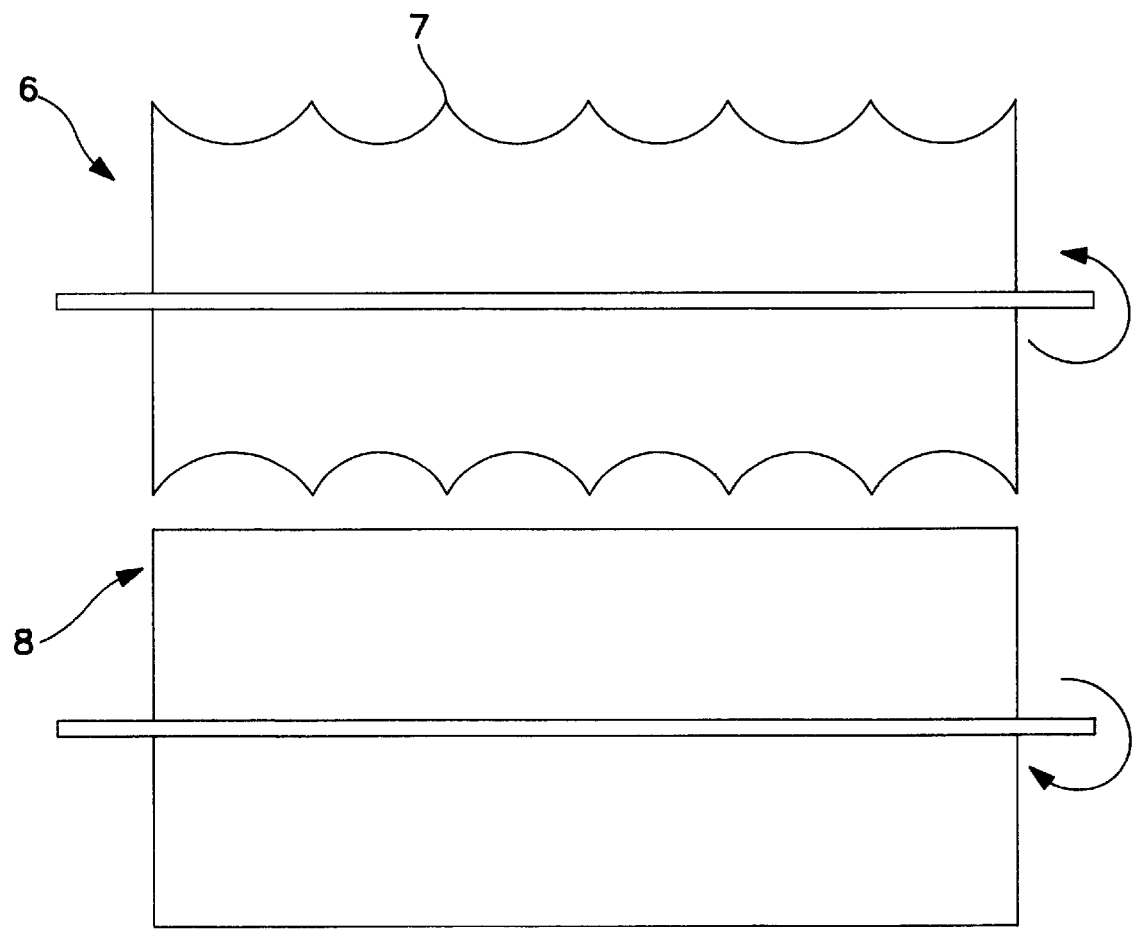
FIG. 6 shows a combination according to the invention of a roll with depressions with a smooth roll.
Figure 7:
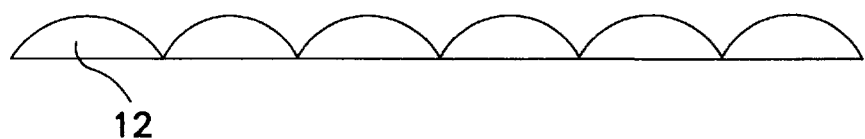
FIG. 7 shows a section through tablets obtained by the roll combination in FIG. 6.

Tablets were produced in a corresponding way using the combination of molding rolls shown in FIG. 6. This resulted in tablets as depicted in FIG. 7.

The calender and molding rolls useful for the present invention can be cooled or heated in a manner known per se and the optimum surface temperature of the rolls for the relevant processing step can be adjusted in this way.

We claim:

1. A process for the production of divisible tablets by molding a melt containing an active ingredient in a calender with two counter-rotating molding rolls which are in contact along a surface line, at least one of the molding rolls having depressions for receiving and molding the melt to tablets, wherein a first molding roll of the two molding rolls is used in which the depressions are divided by n bars, where $n \geq 1$, which bars extend essentially as far as the surface line, and form a score, and as a second molding roll of the two molding rolls there is used either (i) a molding roll with corresponding depressions which are divided by n' bars which bars extend essentially as far as the surface line of the molding roll and form a score, where n' is in the range from 0 to n−1, or (ii) a smooth roll.

2. A process as claimed in claim 1, wherein the first molding roll has depressions with one bar, n=1, and the second molding roll has corresponding depressions without a bar, n'=0.

3. A process as claimed in claim 1, wherein the first molding roll has depressions with two bars, n=2, and the second molding roll has depressions with one bar, n'=1.

4. A process as claimed in claim 1, wherein the melt containing active ingredient is introduced between two sheets of a covering material into the molding rolls so that film-coated tablets or tablets sealed in a blister pack are obtained.

5. A process as claimed in claim 1, wherein the molding rolls have depressions which are elongate or in the shape of a segment of an ellipsoid so that divisible oblong tablets or lenticulr tablets are obtained.

6. An apparatus for carrying out the process of claim 1 comprising two counter-rotating molding rolls (6, 8) which are in contact along a surface line, at least one of the molding rolls having depressions (2) for receiving and molding the melt to tablets wherein the first molding roll (6) has depressions (2) which are divided by n bars, $n \geq 1$, which bars extend essentially up to the surface line and form a score, and the second molding roll (8) either (i) has corresponding depressions (2) which are divided by n' bars which bars extend essentially up to the surface line and form a score, where n' is in the range from 0 to n−1, or (ii) is a smooth roll (8).

7. An apparatus as claimed in claim 6, wherein the first molding roll (6) has depressions (2) with one bar (7), n=1, and the second molding roll (8) has corresponding depressions (2) without a bar, n'=0.

8. An apparatus as claimed in claim 6, wherein the first molding roll (6) has depressions (2) with two bars (7), n=2, and the second molding roll (8) has corresponding depressions (2) with one bar (7), n'-1.

9. An apparatus as claimed in claim 6, wherein the molding rolls (6, 8) have depressions (2) which are elongate or in the shape of a segment of an ellipsoid.

* * * * *